United States Patent [19]
Khanna et al.

[11] Patent Number: 5,696,275
[45] Date of Patent: Dec. 9, 1997

[54] PROCESS FOR THE MANUFACTURE OF PHARMACEUTICAL GRADE RANITIDINE BASE

[75] Inventors: Jag Mohan Khanna; Naresh Kumar; Brij Khera; Purna Chandra Ray, all of New Delhi, India

[73] Assignee: Ranbaxy Laboratories Limited, New Delhi, India

[21] Appl. No.: 265,308

[22] Filed: Jun. 24, 1994

[30]     Foreign Application Priority Data

May 13, 1994 [IN] India ................... 588/DEL/94

[51] Int. Cl.⁶ .................................................. C07D 307/52
[52] U.S. Cl. ................................................. 549/495
[58] Field of Search ........................................ 549/495

[56]            References Cited

U.S. PATENT DOCUMENTS 4,128,658  12/1978  Price et al. ..................... 424/285
4,521,431   6/1985  Crookes ......................... 514/471
4,968,808  11/1990  Mösdorf et al. ................. 548/205

FOREIGN PATENT DOCUMENTS 0 285 681 A1  10/1988  European Pat. Off. .
1565966        4/1980  United Kingdom .

*Primary Examiner*—Ba K. Trinh
*Attorney, Agent, or Firm*—Meltzer, Lippe, Goldstein et al.

[57]            ABSTRACT

A process for the manufacture of pharmaceutical grade ranitidine base(N-[2-[[[5-(Dimethylamino)methyl]-2-furanyl]methyl]thio]ethyl-N'-methyl-2-nitro-1,1-ethenediamine), is described. In-vitro and in-vivo pharmacological studies and acute toxicity studies indicate that it is as active and as safe as Form 2 ranitidine hydrochloride.

28 Claims, 2 Drawing Sheets

5,696,275

PROCESS FOR THE MANUFACTURE OF PHARMACEUTICAL GRADE RANITIDINE BASE

FIELD OF THE INVENTION

This invention relates to a manufacturing process for the $H_2$-antagonist 'ranitidine', that is, N-[2-[[[5-(Dimethylamino) methyl]-2-furanyl]methyl]thio]ethyl-N'-methyl-2-nitro-1,1-ethenediamine in crystalline form having >99.5% purity.

BACKGROUND OF THE INVENTION

Ranitidine hydrochloride, as described and claimed in British Patent Specification No. 1,565,966 (April 1980) shows potent histamine $H_2$-blocking activity. A process for preparing ranitidine is known and described in U.S. Pat. No. 4,128,658 (December 1978) and in British Patent Specification No. 1,565,966 (April 1980). Though a method to prepare crude ranitidine base is described in U.S. Pat. No. 4,128,658 (December 1978), see Example 15 thereby, the ranitidine base produced by this method has not been evaluated for clinical application. In experiments following Example 15, the ranitidine base produced thereby is brownish yellow in color and has a purity of less than 97% (HPLC), with related substances being ca. 2%.

SUMMARY OF THE INVENTION

The present invention provides a process for producing ranitidine base which is crystalline, is of pharmaceutical grade (>99.5% purity), and is convenient to produce on a commercial scale.

According to the invention, a process for preparing pharmaceutical grade ranitidine base comprises reacting a mixture of N-methyl-1-(methylthio)-2-nitroetheneamine and 2-[[[5-(Dimethylamino)methyl-2-furanyl]methyl]thio] ethanamine in water at 40° C. to reflux temperature, removing the unreacted starting material and other impurities at a suitable pH (4–5), preferably by washing, separating the ranitidine base at a suitable pH (9–10), removing water, if any, and precipitating ranitidine base from a "suitable organic solvent", and collecting the resulting product. The product so obtained can be crystallized from a "suitable organic solvent" to produce almost white powder of ranitidine base, having a purity of about 99.6% (HPLC), with related substances being less than 0.4%.

DETAILED DESCRIPTION OF THE INVENTION

Figure 1:
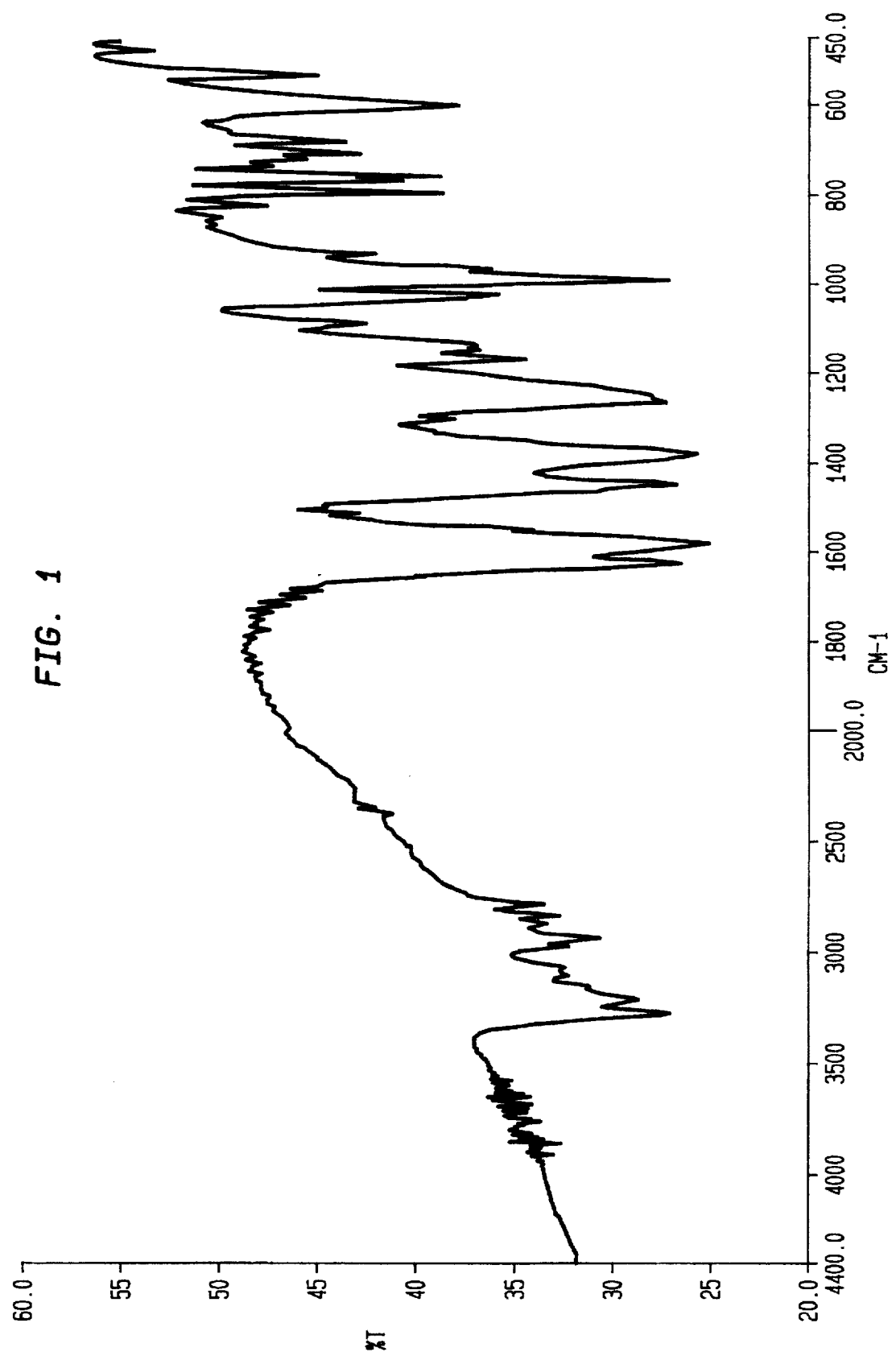
FIG. 1 shows the infra-red spectrum in KBr disc of ranitidine base prepared by the method described in Example 2 below. Ranitidine base prepared this way was also characterized by its proton magnetic resonance spectrum in $CDCl_3$.

In accordance with the present invention, pharmaceutical grade (>99.5% purity) is prepared by reacting a mixture of N-methyl-1-(methylthio)-2-nitroetheneamine and 2-[[[5-(dimethylamino)methyl-2-furanyl]methyl]thio]ethanamine in water at a temperature from about 40° C. to reflux temperature, acidifying the solution to remove unreacted starting materials and other impurities, basifying the solution to separate ranitidine base from the solution, removing water if any, and precipitating the ranitidine base from a suitable organic solvent such as a lower alkanol, and collecting the precipitated ranitidine base. Desirably, the precipitated base is dissolved in a suitable organic solvent and crystallized therefrom.

It has been found that if the ranitidine base is prepared under the above defined working conditions, the following advantages are obtained:

a) the product is easily filtrable and can be readily dried;

b) the solvents used are readily recoverable;

c) the product can be crystallized from the same solvent system;

d) the process is economical and convenient to operate on a commercial scale;

e) the process provides a product which has a high degree of purity (>99.5%); and f) the product is stable.

Generally, the reaction is carried out in water as a medium that has been heated by standard means to a temperature of from about 40° C. to reflux temperature, preferably to about 45°–70° C., most preferably to about 50° C. This temperature is considerably lower than the reaction temperature of the process described in Example 15 of U.S. Pat. No. 4,128,658. The amount of water is at least 1 part by volume per part of the starting material. Higher amounts of water and generally up to 10 parts by volume can be used. Amounts higher than 10 volumes are not useful from an economical point of view because large size apparatus would be necessary.

The reaction will typically be accomplished within about 3 to about 10 hrs, preferably, within 3–4 hours. However, the length of time required will vary depending on such factors as total volume of solution, size of batch and container, temperature of the reaction, and presence or absence of stirring.

The reaction mixture can be acidified to a pH of about 4–5 by means of mineral acids, preferably hydrochloric acid or sulfuric acid, in different concentrations, or organic acids. Unreacted starting material and other impurities can be washed with any water-immiscible solvents like chlorinated hydrocarbons, aromatic hydrocarbons and ketones at different temperatures.

The reaction mixture can be basified to a pH of about 9–10 with basifying agents such as alkali metal carbonates, bicarbonates and hydroxides.

The term "suitable organic solvent" means any lower alkanol and includes those primary, secondary and tertiary alcohols having from one to six carbons atoms, ketones, esters and aliphatic or aromatic hydrocarbons having from one to ten carbon atoms. Mixtures of two or more solvents are also contemplated.

It is also desirable to filter the solution prior to crystal formation in order to remove any insoluble, particulate material. The solutions can be cooled to −10° to 50° C., preferably to about 0°–30° C., most preferably to about 10° C., before precipitation by standard procedures well known in the art.

Addition of a miscible solvent such as hexane, petroleum ether, toluene, ethyl acetate and n-butyl acetate to the solution can be advantageously used to complete crystallization.

Methods known in the art may be used with the process of this invention to enhance any aspect of this process. For example, the solution may be seeded with one or more crystals of ranitidine base prior to the initiation of product crystallization.

Generally, after cooling, the product can be collected by any standard method known in the art such as by filtration, filtration under vacuum, or decantation and drying. Typically, this product will be collected by filtration when any of the solvents within the scope of this process are used.

Ranitidine base prepared as above may further be crystallized using conditions and solvents for crystallizations similar to those described above. Mixtures of two or more solvents are also contemplated.

Histamine $H_2$ antagonist activity of ranitidine base prepared as above has been studied in-vitro by using guinea pig atrium and in-vivo on aspirin induced gastric lesions in conscious rats. Both ranitidine base as well as Form 2 ranitidine hydrochloride were found equi-potent in these tests.

Acute toxicity studies were conducted in mice. From the results of the acute toxicity studies it is concluded that ranitidine base prepared as above is as safe as Form 2 ranitidine hydrochloride.

Ranitidine base prepared as above has been used in formulating the following products:

i) Ranitidine base tablets in two strengths of 150 mg and 300 mg, and
ii) Ranitidine base injection containing 25 mg/ml of the drug. Both strengths of the tablet formulation have been found to have comparable dissolution rates in in-vitro performance to that of Zantac® (Glaxo) which contains Form 2 ranitidine hydrochloride. See FIG. 2.

The accelerated stability of these formulations is satisfactory and long term room temperature studies are currently underway.

The following specific examples are presented to illustrate the inventive process, but they should not be construed as limiting the scope of this invention in any way.

EXAMPLE 1

Preparation of Ranitidine Base

2-[[[5-(Dimethylamino)methyl-2-furanyl]methyl]thio] ethanamine (50 g) and N-methyl-1-(methylthio)-2-nitroetheneamine (40 g) in water (235 ml) was stirred and heated at 45°–50° C. The solution was stirred further for 3–4 hrs. It was acidified with hydrochloric acid and extracted with chloroform. The solution was basified with potassium carbonate and ranitidine base was separated. The water, if any, was removed by azeotropic distillation under reduced pressure at 40°–45° C. using isopropanol. The resultant solution was cooled to 10° C. and n-hexane (500 ml) was added. Ranitidine base was filtered off and dried under vacuum to give the crude product (66.2 g), m.p. 68°–70° C.; purity=99.4% (HPLC); IR(KBr): 3280, 3200, 2820, 2774, 1620, 1580, 1440, 1370, 1258, 1130, 1020, 990, 820, 790, 760, 680 and 600 cm$^{-1}$; $\delta_H$(CDCl$_3$):2.23 [6H,s, —N(CH$_3$)$_2$], 2.75(2H, t, —SCH$_2$CH$_2$), 2.85(3H,br d, CH$_3$NH—), 3.3 (2H,2t, —CH$_2$NH—), 3.4(2H,s, >NCH$_2$), 3.7 (2H,s, CH$_2$ bridge linking), 6.0–6.2 (2H,AB,furan) and 6.5 (,1H,s,=CHNO$_2$).

EXAMPLE 2

The process of Example 1 was repeated at a commercial scale, using 2-[[[5-(Dimethylamino)methyl-2-furanyl] methyl]thio]ethanamine (35 kg) and N-methyl-1-(methylthio)-2-nitroetheneamine (28 kg) to give crude ranitidine base (46.5 kg), m.p. 68°–70° C.; purity—99.1% (HPLC).

EXAMPLE 3

The process of Example 1 was repeated at 25 g scale, using a mixture of ethyl acetate and isopropanol instead of isopropanol to give ranitidine base (34.5 g), m.p. 67°–69° C.; purity=98.8% (HPLC).

EXAMPLE 4

2- [[[5-(Dimethylamino)methyl-2-furanyl]methyl]thio] ethanamine (25 g) and N-methyl-1-(methylthio)-2-nitroetheneamine (18 g) in water (35 ml) was stirred and heated at 50° C. The solution was stirred further for 3–4 hrs. It was acidified with sulfuric acid and extracted with chloroform. The solution was basified with potassium carbonate and ranitidine base was separated. The water, if any, was removed by azeotropic distillation under reduced pressure at 40°–45° C. using isopropanol. The resultant solution was cooled to 10° C. and n-hexane (250 ml) was added. Ranitidine base was filtered off and dried under vacuum to give the crude product (30 g), m.p. 67°–69° C., purity=99.1% (HPLC)

EXAMPLE 5

2-[[[5-(Dimethylamino)methyl-2-furanyl]methyl]thio] ethanamine (25 g) and N-methyl-1-(methylthio)-2-nitroetheneamine (20 g) in water (118 ml) was stirred and heated at 50° C. The solution was stirred further for 3–4 hrs. It was acidified with sulfuric acid and extracted with chloroform. The solution was basified with potassium carbonate and ranitidine base was extracted with chloroform and worked up. Isopropanol was added to the residue, cooled to 10° C., and n-hexane (250 ml) was added. Ranitidine base was filtered off and dried under vacuum to give the crude product (33 g), m.p. 67°–69° C.; purity=99% (HPLC)

EXAMPLE 6

Crystallization of Ranitidine Base

Ranitidine base (25 g) prepared earlier was crystallized by dissolving in isopropanol at 35°–40° C. and precipitating from n-hexane. The slurry was cooled to 10° C. and stirred for 1–2 hrs. The product was filtered off, washed with n-hexane, and dried to give pure ranitidine base (21 g), m.p. 71°–72° C.; purity=99.6% (HPLC)

EXAMPLE 7

The process of Example 5 was repeated using isobutanol instead of isopropanol at 5 g scale to give pure ranitidine base (3.9 g), m.p. 71°–72° C.; purity=99.8% (HPLC)

EXAMPLE 8

Ranitidine base (150 g) prepared earlier was crystallized by dissolving in toluene at 38°–40° C. The resultant solution was cooled to 10° C. and the slurry was stirred for 1 hour at 10°–12° C. The product was filtered off, washed with pre-cooled toluene and dried under vacuum to give pure ranitidine base (135 g), m.p. 70°–71° C.; purity=99.8% (HPLC)

EXAMPLE 9

The process of Example 7 was repeated, using ethyl acetate instead of toluene to give pure ranitidine base (137 g), m.p. 70°–71° C.; purity=99.8% (HPLC)

EXAMPLE 10

The process of Example 7 was repeated, using 4-methylpentan-2-one instead of toluene to give pure ranitidine base (120 g), m.p. 71°–72° C.; purity=99.7% (HPLC)

It is believed that the higher purity ranitidine base produced by the process of the present invention in comparison to the method described in Example 15 of U.S. Pat. No. 4,128,658, may be attributed to one or more of the following combination of factors:

(1) reaction under higher dilution of reaction medium, i.e., water, thereby producing fewer impurities;

(2) higher molar concentration (1.157:1) of one of the starting materials, i.e., N-methyl-1-(methylthio)-2-nitroetheneamine, with respect to 2-[[[5-(Dimethylamino)methyl-2-furanyl]methyl]thio]ethanamine, as against a ratio of 1.036:1 in Example 15 of U.S. Pat. No. 4,128,658;

(3) shorter reaction time (ca. 3–4 hours) than in Example 15 of U.S. Pat. No. 4,128,658, which reduces the quantity of impurities formed, and monitoring of the completion of the reaction by TLC;

(4) removal of excess starting materials and impurities by extraction at a suitable pH; and (5) recrystallization of the crude ranitidine base to give a higher purity final product.

While the invention has been described by reference to specific embodiments, this was for purposes of illustration only. Numerous alternative embodiments will be apparent to those skilled in the art and are considered to be within the scope of the invention.

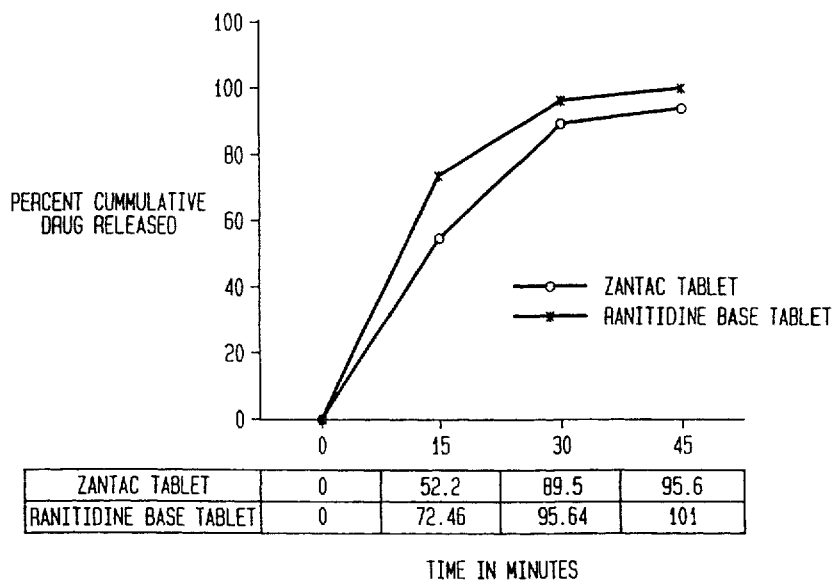

We claim:

1. A process for preparing pharmaceutical grade ranitidine base comprising reacting a mixture of N-methyl-1-(methylthio)-2-nitroetheneamine and 2-[[[5-(dimethylamino)methyl-2-furanyl]methyl]thio]ethanamine in a water solution at a temperature from about 40° C. to reflux temperature, adjusting the pH of said solution a first time to a pH in the range of about 4–5 to remove unreacted starting materials and impurities from said solution, adjusting the pH of said solution a second time to a pH in the range of about 9–10 to separate ranitidine base from said solution, removing water if any and precipitating ranitidine base from an organic solvent, and collecting said precipitated ranitidine base.

2. The process of claim 1 wherein said first pH adjustment to remove unreacted starting materials and impurities from said solution comprises adding an acid to said solution.

3. The process of claim 2 wherein said acid is a mineral acid or an organic acid.

4. The process of claim 3 wherein said acid is hydrochloric acid or sulfuric acid.

5. The process of claim 4 further comprising removing said unreacted starting material and other impurities after said first pH adjustment by washing said solution with a water-immiscible solvent.

6. The process of claim 5 wherein said water immiscible solvent is a chlorinated hydrocarbon, aromatic hydrocarbon, or ketone.

7. The process of claim 6 wherein said water-immiscible solvent is dichloromethane, chloroform, or 1,2-dichloroethane.

8. The process of claim 1 wherein said second pH adjustment to separate ranitidine base from said solution comprises adding a basifying agent to said solution.

9. The process of claim 8 wherein said basifying agent is an alkali metal carbonate, alkali metal bicarbonate, or alkali metal hydroxide.

10. The process of claim 9 wherein said alkali metal is sodium or potassium.

11. The process of claim 8 wherein said basifying agent is ammonium carbonate, ammonium bicarbonate, or ammonium hydroxide.

12. The process of claim 1 wherein said organic solvent is a lower alkanol.

13. The process of claim 1 wherein said organic solvent is a primary alcohol, a secondary alcohol, a tertiary alcohol, a ketone, an ester, a saturated aromatic hydrocarbon, or an unsaturated aromatic hydrocarbon.

14. The process of claim 1 wherein said solvent is n-propanol, isopropanol, isobutanol, n-butanol, ethylmethyl ketone, 4-methyl pentan-2-one, ethyl acetate, n-butyl acetate, toluene, or cyclohexane.

15. The process of claim 1 further comprising adding an additional organic solvent to complete crystallization of said ranitidine base product.

16. The process of claim 1 wherein said additional organic solvent is hexane, petroleum ether, toluene, ethyl acetate, or n-butyl acetate.

17. The process of claim 16 wherein said additional organic solvent is hexane or petroleum ether.

18. The process of claim 1 further comprising dissolving said collected ranitidine base in an additional organic solvent and crystallizing ranitidine base from said additional organic solvent.

19. The process of claim 18 wherein said additional organic solvent is an alkanol.

20. The process of claim 18 wherein said additional organic solvent is a primary alcohol, a secondary alcohol, a tertiary alcohol, a ketone, an ester, a saturated hydrocarbon, or an unsaturated hydrocarbon.

21. The process of claims 18 further comprising adding a further organic solvent to complete crystallization of said ranitidine base from said additional organic solvent.

22. The process of claim 21 wherein said further organic solvent is hexane or petroleum ether.

23. A process for preparing pharmaceutical grade ranitidine base comprising reacting a mixture of N-methyl-1-(methylthio)-2-nitroetheneamine and 2-[[[5-(dimethylamino) methyl-2-furanyl]methyl]thio]ethanamine in a water solution at a temperature from about 40° C. to reflux temperature, adding sufficient acidifying agent to adjust the pH of said solution to a pH range of about 4–5, removing unreacted starting materials and impurities from said solution, adding a basifying agent to said solution to adjust the pH of said solution to a pH in the range of about 9–10, extracting ranitidine base from said solution by washing said solution with an organic solvent, and precipitating ranitidine base from said organic solvent.

24. The process of claim 23 wherein said unreacted starting materials are removed from said solution by washing said solution with a water-immiscible solvent.

25. The process of claim 23 further comprising removing water if any from said organic solvent by azeotropic distillation.

26. The process of claim 23 further comprising adding an additional organic solvent to said organic solvent to cause crystallization of said ranitidine base.

27. The process of claim 23 wherein said acidifying agent is a mineral acid or an organic acid.

28. The process of claim 23 wherein said basifying agent is an alkali metal or ammonium carbonate, bicarbonate, or hydroxide.

* * * * *

UNITED STATES PATENT AND TRADEMARK OFFICE
CERTIFICATE OF CORRECTION

PATENT NO. : 5,696,275
DATED : Dec. 9, 1997
INVENTOR(S) : Jag Mohan Khanna, et al It is certified that error appears in the above-identified patent and that said Letters Patent is hereby corrected as shown below:

The title page, should be deleted to be replaced with the attached title page.

Figure 2:
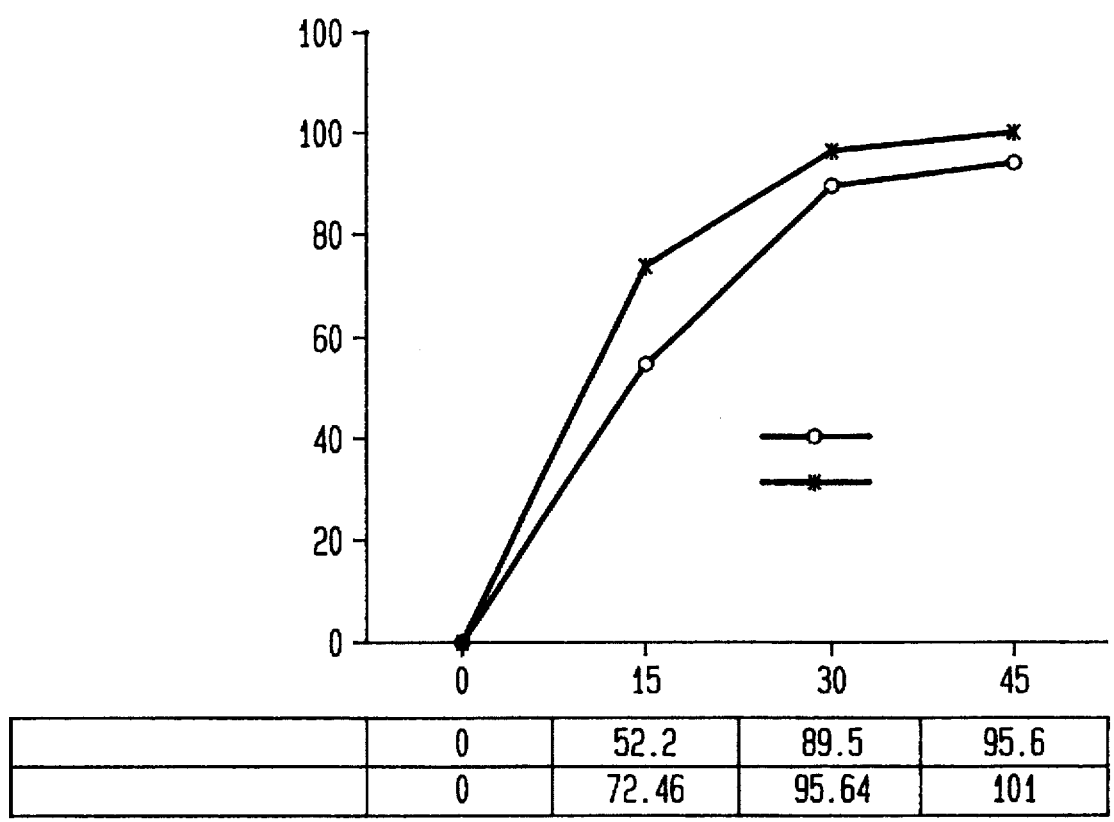
FIG. 2 shows a comparative dissolution profile (dissolution parameters as per USP) of Zantac® (Glaxo) 300 mg tablet vs. 300 mg tablet of ranitidine base prepared in accordance with the present invention.

The drawing sheet, consisting of Fig. 2. Should be deleted to be replaced with the attached drawing sheet.

Signed and Sealed this

Twenty-eighth Day of April, 1998

Attest:

BRUCE LEHMAN

Attesting Officer

Commissioner of Patents and Trademarks

United States Patent [19]

Khanna et al.

[11] Patent Number: 5,696,275
[45] Date of Patent: Dec. 9, 1997

[54] PROCESS FOR THE MANUFACTURE OF PHARMACEUTICAL GRADE RANITIDINE BASE

[75] Inventors: Jag Mohan Khanna; Naresh Kumar; Brij Khera; Purna Chandra Ray, all of New Delhi, India

[73] Assignee: Ranbaxy Laboratories Limited, New Delhi, India

[21] Appl. No.: 265,308

[22] Filed: Jun. 24, 1994

[30] Foreign Application Priority Data

May 13, 1994 [IN] India .................. 588/DEL/94

[51] Int. Cl.$^6$ .................. C07D 307/52
[52] U.S. Cl. .................. 549/495
[58] Field of Search .................. 549/495

[56] References Cited

U.S. PATENT DOCUMENTS 4,128,658  12/1978  Price et al. .................. 424/285
4,521,431  6/1985  Crookes .................. 514/471
4,968,808  11/1990  Mösdorf et al. .................. 548/205

FOREIGN PATENT DOCUMENTS 0 285 681 A1  10/1988  European Pat. Off.
1565966  4/1980  United Kingdom

*Primary Examiner*—Ba K. Trinh
*Attorney, Agent, or Firm*—Meltzer, Lippe, Goldstein et al.

[57] ABSTRACT

A process for the manufacture of pharmaceutical grade ranitidine base(N-[2-[[[5-(Dimethylamino)methyl]-2-furanyl]methyl]thio]ethyl-N'-methyl-2-nitro-1,1-ethenediamine), is described. In-vitro and in-vivo pharmacological studies and acute toxicity studies indicate that it is as active and as safe as Form 2 ranitidine hydrochloride.

28 Claims, 2 Drawing Sheets

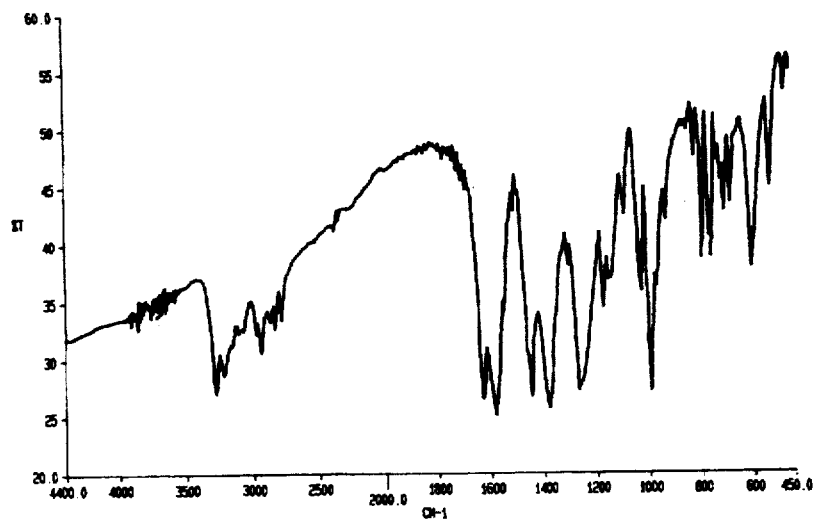

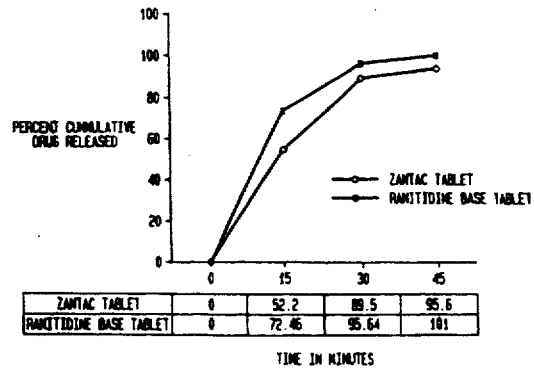

UNITED STATES PATENT AND TRADEMARK OFFICE
CERTIFICATE OF CORRECTION

PATENT NO. : 5,696,275  
DATED : December 9, 1997  
INVENTOR(S) : Jag Mohan Khanna; Naresh Kumar; Brij Khera; Purna Chandra Ray Page 3 of 3

It is certified that error appears in the above-indentified patent and that said Letters Patent is hereby corrected as shown below: